US012631527B2

(12) United States Patent
Chen

(10) Patent No.: US 12,631,527 B2
(45) Date of Patent: May 19, 2026

(54) ISOLATION CHIP ASSEMBLY

(71) Applicant: Shenzhen Huixin Life Technologies Co., Ltd, Shenzhen (CN)

(72) Inventor: Yuchao Chen, Rodeo, CA (US)

(73) Assignee: Shenzhen Huixin Life Technologies Co., Ltd, Shenzhen (CN)

( * ) Notice: Subject to any disclaimer, the term of this patent is extended or adjusted under 35 U.S.C. 154(b) by 957 days.

(21) Appl. No.: 17/767,594

(22) PCT Filed: Nov. 11, 2020

(86) PCT No.: PCT/CN2020/128176
§ 371 (c)(1),
(2) Date: Apr. 8, 2022

(87) PCT Pub. No.: WO2022/099517
PCT Pub. Date: May 19, 2022

(65) Prior Publication Data
US 2023/0160795 A1 May 25, 2023

(51) Int. Cl.
*G01N 1/34* (2006.01)
*C12M 1/26* (2006.01)
*G01N 1/40* (2006.01)

(52) U.S. Cl.
CPC .............. *G01N 1/34* (2013.01); *C12M 33/14* (2013.01); *G01N 2001/4088* (2013.01)

(58) Field of Classification Search
CPC . G01N 1/34; G01N 2001/4088; C12M 33/14; C12M 35/04; C12M 47/04; C12M 29/04
USPC ....................................................... 435/288.1
See application file for complete search history.

(56) References Cited

U.S. PATENT DOCUMENTS

| | | | |
|---|---|---|---|
| 9,738,918 B2 * | 8/2017 | Alburty ............... | G01N 1/4005 |
| 10,161,926 B2 * | 12/2018 | Gilmanshin ....... | G01N 15/1459 |
| 2003/0134416 A1 * | 7/2003 | Yamanishi ......... | G01N 15/0272 |
| | | | 435/372 |
| 2006/0027686 A1 | 2/2006 | Taylor et al. | |
| 2016/0237397 A1 | 8/2016 | Guia et al. | |

(Continued)

FOREIGN PATENT DOCUMENTS

| | | |
|---|---|---|
| CN | 103506013 A | 1/2014 |
| CN | 104703699 A | 6/2015 |
| CN | 207478341 U | 6/2018 |

(Continued)

*Primary Examiner* — Michael L Hobbs
*Assistant Examiner* — Lenora A Abel
(74) *Attorney, Agent, or Firm* — ScienBiziP, P.C.

(57) ABSTRACT

An isolation chip assembly includes an isolation chip (10), first oscillators (20), and second oscillators (30). The isolation chip (10) includes a sample reservoir (13), a first filtration membrane (14) and a second filtration membrane (16) at opposite sides of the sample reservoir (13). The first oscillators (20) are mounted on the first filtration membrane (14) and the second filtration membrane (16), and can generate a first oscillation wave when operating. The second oscillators (30) are mounted on outer surfaces of the first chamber (15) and the second chamber (17), and can generate a second oscillation wave when operating. A frequency of the first oscillation wave is greater than a frequency of the second oscillation wave, and an amplitude of the first oscillation wave is less than an amplitude of the second oscillation wave.

7 Claims, 6 Drawing Sheets

(56) References Cited

U.S. PATENT DOCUMENTS

2019/0160432 A1* 5/2019 Chen ................ G01N 33/57488

FOREIGN PATENT DOCUMENTS

| | | | | | |
|---|---|---|---|---|---|
| CN | 211784638 | U | 10/2020 | | |
| KR | 10-2016-0050040 | A | 5/2016 | | |
| WO | WO-2005031300 | A2 * | 4/2005 | ............ | B03C 5/026 |
| WO | 2020/191452 | A1 | 10/2020 | | |

* cited by examiner

ISOLATION CHIP ASSEMBLY

FIELD

The subject matter herein generally relates to biotechnology, and more particularly, to an isolation chip assembly for isolation and purification of target particles from a liquid sample.

BACKGROUND

Exosomes are small vesicles with a double phospholipid membrane structure, and has a diameter of 30-150 nm continuously secreted by living cells. As a carrier of intercellular communication, the exosomes carry specific components such as proteins, nucleic acids, and metabolic small molecules from mother cells. A large number of studies have shown that the exosomes are involved in a variety of events in tumor development, including immune escape, angiogenesis, tumor metastasis, tumor drug resistance, and so on. Exocrine can be released by cancer cells earlier and continuously and enter the patient's blood circulation system. The double phospholipid membrane structure can effectively protect the carried proteins and encapsulated nucleic acids. The exosomes widely and stably exist in a variety of clinical samples, including blood, urine, ascites, tissue fluid, tears, saliva, and cerebrospinal fluid. There are many exosomes in blood and urine, so it is easy to obtain clinical samples. Therefore, the exosomes are considered to be the key research objects in the field of in vitro diagnosis and clinical detection of tumors, and are expected to play a great clinical value in early diagnosis of tumors, evaluation of tumor metastasis and recurrence, evaluation of tumor heterogeneity, dynamic detection of tumor occurrence, development and curative effect, detection of drug-resistant mutations, personalized drug use, and so on.

At present, a main obstacle to the clinical application of the exosomes is that the filtration membrane is blocked during an isolation process, and the isolation has low flux and low purity.

SUMMARY

Therefore, an isolation chip assembly for overcome the above shortcomings is needed.

The present disclosure provides an isolation chip assembly for isolation and purification of target particles from a liquid sample. The isolation chip assembly includes an isolation chip, first oscillators, and second oscillators. The isolation chip includes a sample reservoir, and a first filtration membrane and a second filtration membrane disposed at opposite sides of the sample reservoir. Sizes of pores of each of the first filtration membrane and the second filtration membrane are smaller than sizes of the target particles. The isolation chip further includes a first chamber and a second chamber, the first chamber is connected to the sample reservoir through the first filtration membrane, the second chamber is connected to the sample reservoir through the second filtration membrane. The first oscillators are mounted on the first filtration membrane and the second filtration membrane, and can generate a first oscillation wave when operating. The second oscillators are mounted on outer surfaces of the first chamber and the second chamber, and can generate a second oscillation wave when operating. A frequency of the first oscillation wave is greater than a frequency of the second oscillation wave, an amplitude of the first oscillation wave is less than an amplitude of the second oscillation wave.

In some possible implementations, the frequency of the first oscillation wave is 5000 Hz to 8000 Hz; the frequency of the second oscillation wave is 100 Hz to 500 Hz.

In some possible implementations, the frequency of the first oscillation wave is equal to a resonance frequency of the first filtration membrane or the second filtration membrane.

In some possible implementations, the first oscillators and the second oscillators are located on a same horizontal plane.

In some possible implementations, the isolation chip further includes a first side cover and a second side cover, the first side cover includes a first cover body, and a first barrier sheet and a second barrier sheet located on opposite sides of the first cover body, the first filtration membrane is fixed between the first barrier sheet and the second barrier sheet, and faces the first cover body, the first cover body, the first barrier sheet, the second barrier sheet, and the first filtration membrane cooperatively define the first chamber; the second side cover includes a second cover body, and a third barrier sheet and a fourth barrier sheet located on opposite sides of the second cover body, the third barrier sheet faces the first barrier sheet, the fourth barrier sheet faces the second barrier sheet, the second filtration membrane is fixed between the third barrier sheet and the fourth barrier sheet, and faces the second cover body, the second cover body, the third barrier sheet, the fourth barrier sheet, and the second filtration membrane cooperatively define the second chamber; the sample reservoir is disposed between the first filtration membrane and the second filtration membrane.

In some possible implementations, the second oscillators are fixed to outer surfaces of the first cover body and the second cover body.

In some possible implementations, the first chamber defines a first outlet that connects the first chamber to an ambient environment; the second chamber defines a second outlet that connects the second chamber to the ambient environment.

In some possible implementations, each of the first oscillators is a harmonic oscillator.

In some possible implementations, each of the second oscillators is a vibrating motor.

Compared to the existing device, the first oscillators of the present disclosure can transmit the first oscillation wave to the first filtration membrane and the second filtration membrane, so that the target particles adsorbed in the pores of the filtration membranes can be quickly separated from the pores of the filtration membranes and resuspended in the liquid sample. The second oscillators can transmit the second oscillation wave, and the second oscillation wave and the first oscillation wave can cooperatively disturb the liquid sample and the filtration membranes to generate an acoustic streaming, which prevents the target particles from clogging the pores or from gathering together, and improves the isolation and purification efficiency.

Figure 1:
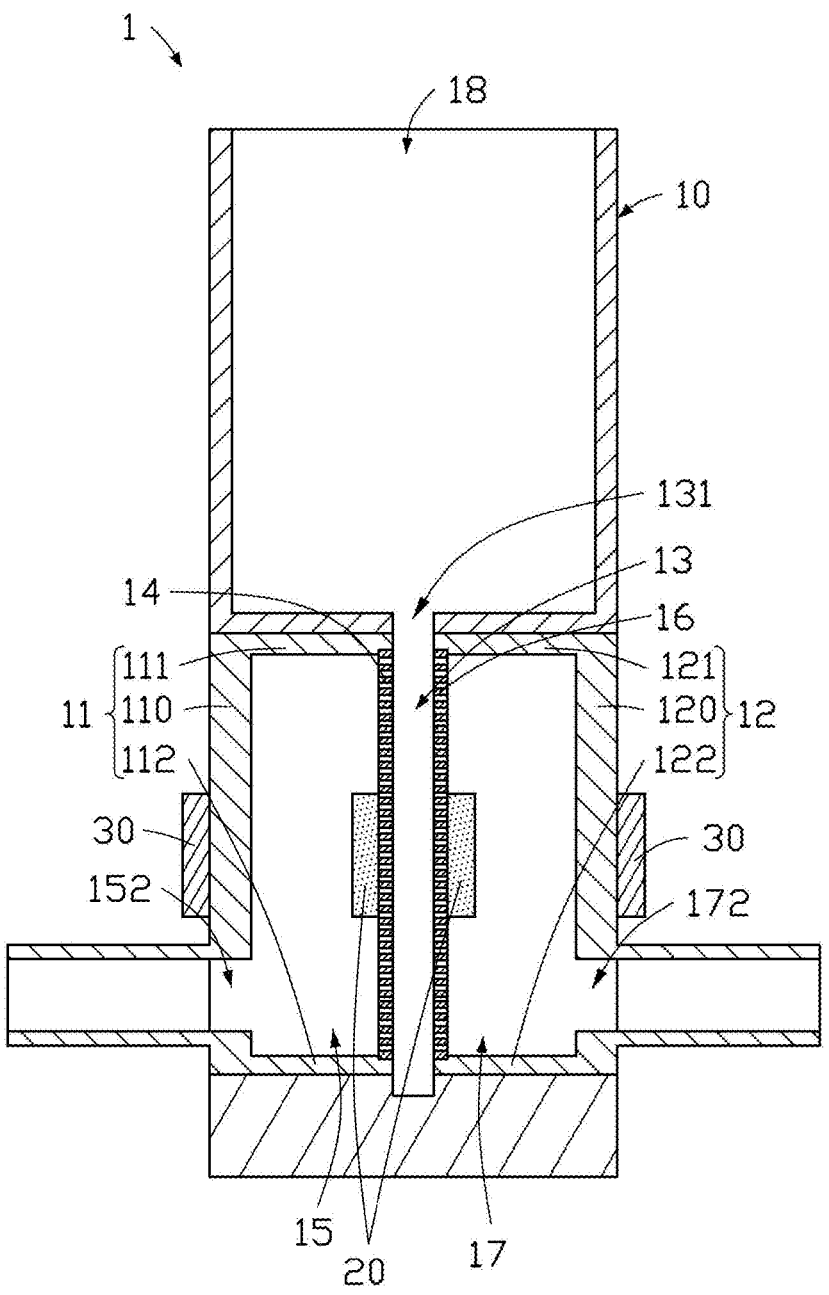
FIG. 1 is a diagrammatic view of an embodiment of an isolation chip assembly according to the present disclosure.

Main Description of Component Symbols:

Isolation chip assembly 1; isolation chip 10; first side cover 11; second side cover 12; sample reservoir 13; first filtration membrane 14; first chamber 15; second filtration membrane 16; second chamber 17; sample adding chamber 18; first oscillator 20; second oscillator 30; frequency converting module 40; vacuum system 50; controller 60; isolation device 100; first cover body 110; first barrier sheet 111; second barrier sheet 112; second cover body 120; third barrier sheet 121; fourth barrier sheet 122; sample injection inlet 131; first outlet 152; second outlet 172; frequency converter 410; valve 420; first vacuum pump 510; second vacuum pump 520.

Implementations of the present disclosure will now be described, by way of embodiments only, with reference to the attached figures.

DETAILED DESCRIPTION

The technical solution of this application will be described below in combination with embodiments and examples of this application. It should be noted that when a unit is described as "connected to" another unit, the unit can either be directly connected to the another unit, or an intermediate unit may exist therebetween. When a unit is described as "disposed on" another unit, the unit may be set directly on another unit, or an intermediate unit may exist therebetween. Unless otherwise defined, all technical and scientific terms used herein have the same meaning as those skilled in the art. The names of components or devices used in the application are for describing the specific embodiments, but are not intended to limit the scope of the application.

FIG. 1 illustrates an embodiment of an isolation chip assembly 1 adapted for isolation and purification of different particles from a liquid sample, so as to obtain target particles of particularly sizes. The liquid sample can be a bioliquid such as plasma, serum, saliva, urine, and lavage. The target particles can be biological cells such as circulating tumor cells (CTCs) or exosomes. The isolation chip assembly 1 includes an isolation chip 10, a first oscillator 20, and a second oscillator 30.

The isolation chip 10 includes a sample reservoir 13, and a first filtration membrane 14 and a second filtration membrane 16 at opposite sides of the sample reservoir 13. The sizes of the pores of the first filtration membrane 14 and the pores of the second filtration membrane 16 are smaller than the size of the target particles.

Furthermore, the isolation chip 10 further includes a first chamber 15 and a second chamber 17. The first chamber 15 is connected to the sample reservoir 13 by the first filtration membrane 14. The first chamber 15 includes a first outlet 152 that connects the first chamber 15 to an ambient environment. The second chamber 17 is connected to the sample reservoir 13 by the second filtration membrane 16. The second chamber 17 includes a second outlet 172 that connects the second chamber 17 to the ambient environment. The first chamber 15 and the second chamber 17 can be positioned at the opposite sides of the sample reservoir 13.

In use, the liquid sample is added to the sample reservoir 13. Each of the first outlet 152 and the second outlet 172 is connected to a vacuum system 50 (shown in FIG. 4). When the vacuum system 50 evacuates the first chamber 15 through the first outlet 152, a negative pressure is generated in the first chamber 15. Under the negative pressure in the first chamber 15, compositions in the liquid sample that are smaller than the pores of the first filtration membrane 14 (including small particles and liquid) can flow towards the first filtration membrane 14 and then enter the first chamber 15 through the first filtration membrane 14. When the vacuum system 50 evacuates the second chamber 17 through the second outlet 172, a negative pressure is generated in the second chamber 17. Under the negative pressure in the second chamber 17, compositions in the liquid sample that are smaller than the pores of the second filtration membrane 16 can flow towards the second filtration membrane 16 and then enter the second chamber 17 through the second filtration membrane 16. At the same time, the back flow of the liquid sample adjacent to the first filtration membrane 14 prevents any composition from accumulating in the pores of the first filtration membrane 14. Thus, clogging of the first filtration membrane 14 can be avoided. Since the negative pressure is alternately applied in the first chamber 15 and the second chamber 17, the compositions in the liquid sample can alternately flow through the first filtration membrane 14 and the second filtration membrane 16. This leaves the particles that are larger than the pores of the first filtration membrane 14 and the second filtration membrane 16 (that is, the target particles) in the sample reservoir 13. The design of the isolation chip 10 makes the components adsorbed on the first filtration membrane 14 and the second filtration membrane 16 easy to be separated therefrom under the alternated negative pressures, which can effectively prevent the pores of the filter membrane from being blocked.

Figure 2:
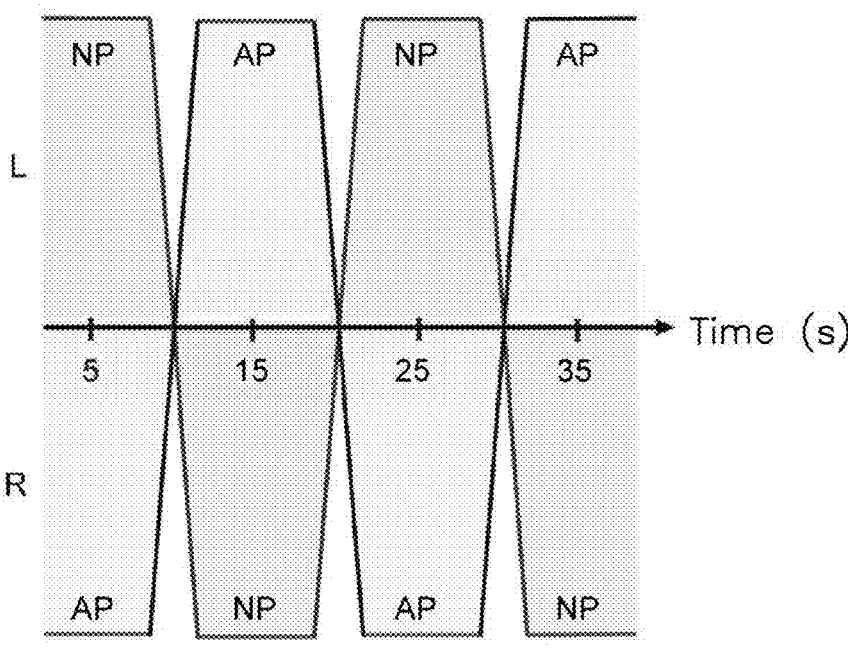
FIG. 2 is a diagrammatic view showing a negative pressure applied on the isolation chip assembly of FIG. 1.

Referring to FIG. 2, in an embodiment, the negative pressure (NP) alternating between the first chamber 15 and the second chamber 17 is caused by trapezoidal wave shaped pulse signals. The trapezoidal wave shaped pulse signals have an amplitude of 10 $V_{pp}$, and a frequency of 5000 Hz to 7000 Hz. The trapezoidal wave shaped pulse signal can avoid damage to the first filtration membrane 14 and the second filtration membrane 16 caused by sudden change of direction of the negative pressure. Since a high protein concentration is included in a plasma sample, to further avoid the clogging of the filtration membranes, an air pressure (AP) can be applied to one chamber when the negative pressure is applied to the other chamber, thereby improving the back flow at the filtration membranes.

Referring to FIG. 1, two first oscillators 20 are included. One of the first oscillators 20 is mounted on a surface of the first filtration membrane 14 away from the second filtration membrane 16. The other one of the first oscillators 20 is mounted on a surface of the second filtration membrane 16 away from the first filtration membrane 14. The first oscillators 20 can generate a first horizontal oscillation wave when operating, and then transmit the first oscillation wave to the first filtration membrane 14 and the second filtration membrane 16 to drive the first filtration membrane 14 and the second filtration membrane 16 to vibrate at a high frequency. Therefore, the target particles adsorbed in the pores of the filtration membranes can be quickly separated from the pores of the filtration membranes and resuspended in the liquid sample, thereby further avoiding the clogging of the filtration membranes and obtaining an efficient isolation.

Figure 3:
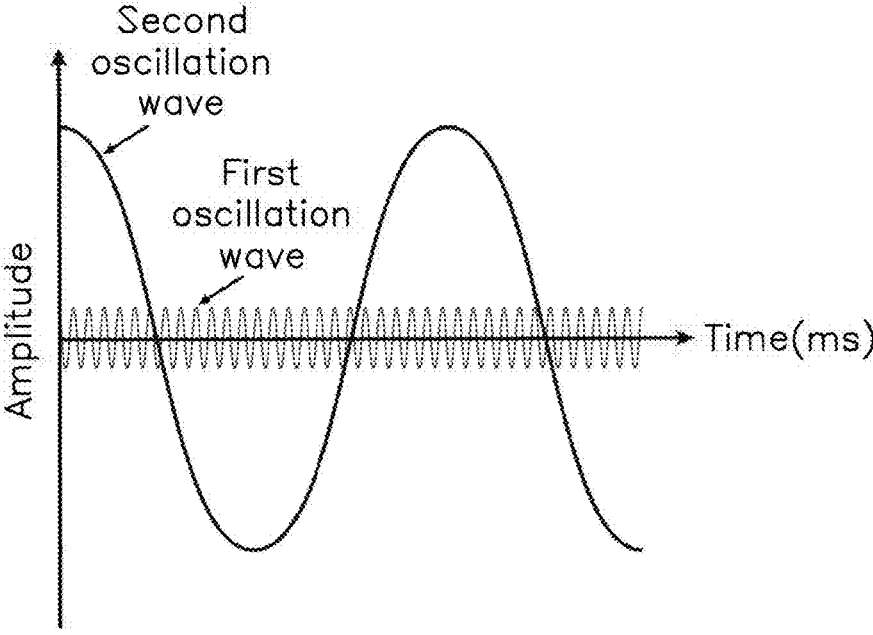
FIG. 3 is a diagrammatic view showing a first oscillation wave and a second oscillation wave applied to the isolation chip assembly of FIG. 1.

Two second oscillators 30 are included. One of the second oscillators 30 is mounted on an outer surface of the first chamber 15. The other one of the second oscillators 30 is mounted on an outer surface of the second chamber 17. The second oscillators 30 can generate a second horizontal oscillation wave when operating. Referring to FIG. 3, the frequency of the first oscillation wave is greater than the frequency of the second oscillation wave, but the amplitude of the first oscillation wave is less than the amplitude of the second oscillation wave. The second oscillation wave is transmitted to the whole isolation chip 10 through the first chamber 15 and the second chamber 17, thus the isolation chip 10 can vibrate at a low frequency. The first oscillation wave and the second oscillation wave can cooperatively disturb the liquid sample and the filtration membranes to generate an acoustic streaming, which prevents the target particles from clogging the pores or from gathering together, and improves the isolation and purification efficiency. In at least one embodiment, the first oscillator 20 may be a harmonic oscillator, and the second oscillator 30 may be a vibrating motor.

In at least one embodiment, the frequency of the first oscillation wave is 5000 Hz to 8000 Hz. The frequency of the second oscillation wave is 100 Hz to 500 Hz. Neither the first oscillation wave nor the second oscillation wave at such frequency will cause damage to the target particles. In at least one embodiment, the frequency of the first oscillation wave can be approximately the same as the resonance frequency of the first filtration membrane 14 or the second filtration membrane 16. Thus, the first filtration membrane 14 or the second filtration membrane 16 can vibrate with a larger amplitude, thereby causing the target particles adsorbed on the filtration membranes to be separated from the filtration membranes more quickly.

In at least one embodiment, the first oscillators 20 and second oscillators 30 are located on a same horizontal plane. That is, the first oscillation wave and the second oscillation wave are towards a same direction, so that the first oscillation wave and the second oscillation wave can be superimposed on each other to form a coordinated oscillation wave.

In at least one embodiment, the isolation chip 10 further includes a first side cover 11 and a second side cover 12. The first side cover 11 includes a first cover body 110, and a first barrier sheet 111 and a second barrier sheet 112 located on opposite sides of the first cover body 110. The first filtration membrane 14 is fixed between the first barrier sheet 111 and the second barrier sheet 112, and faces the first cover body 110. The first cover body 110, the first barrier sheet 111, the second barrier sheet 112, and the first filtration membrane 14 cooperatively define the first chamber 15. The second side cover 12 includes a second cover body 120, and a third barrier sheet 121 and a fourth barrier sheet 122 located on opposite sides of the second cover body 120. The third barrier sheet 121 faces the first barrier sheet 111. The fourth barrier sheet 122 faces the second barrier sheet 112. The second filtration membrane 16 is fixed between the third barrier sheet 121 and the fourth barrier sheet 122, and faces the second cover body 120. The second cover body 120, the third barrier sheet 121, the fourth barrier sheet 122, and the second filtration membrane 16 cooperatively define the second chamber 17. The sample reservoir 13 is disposed between the first filtration membrane 14 and the second filtration membrane 16. The second oscillator 30 is fixed to an outer surface of the first cover body 110 or the second cover body 120.

Furthermore, the first barrier sheet 111 and the third barrier sheet 121 are spaced from each other to define a sample injection inlet 131 that communicates with the sample reservoir 13. The isolation chip 10 further includes a sample adding chamber 18 that communicates with the sample reservoir 13 through the sample injection inlet 131. During use, the liquid sample is added to the sample adding chamber 18, and the sample injection inlet 131 allows the liquid sample in the sample adding chamber 18 to flow out and enter the sample reservoir 13.

Figure 4:
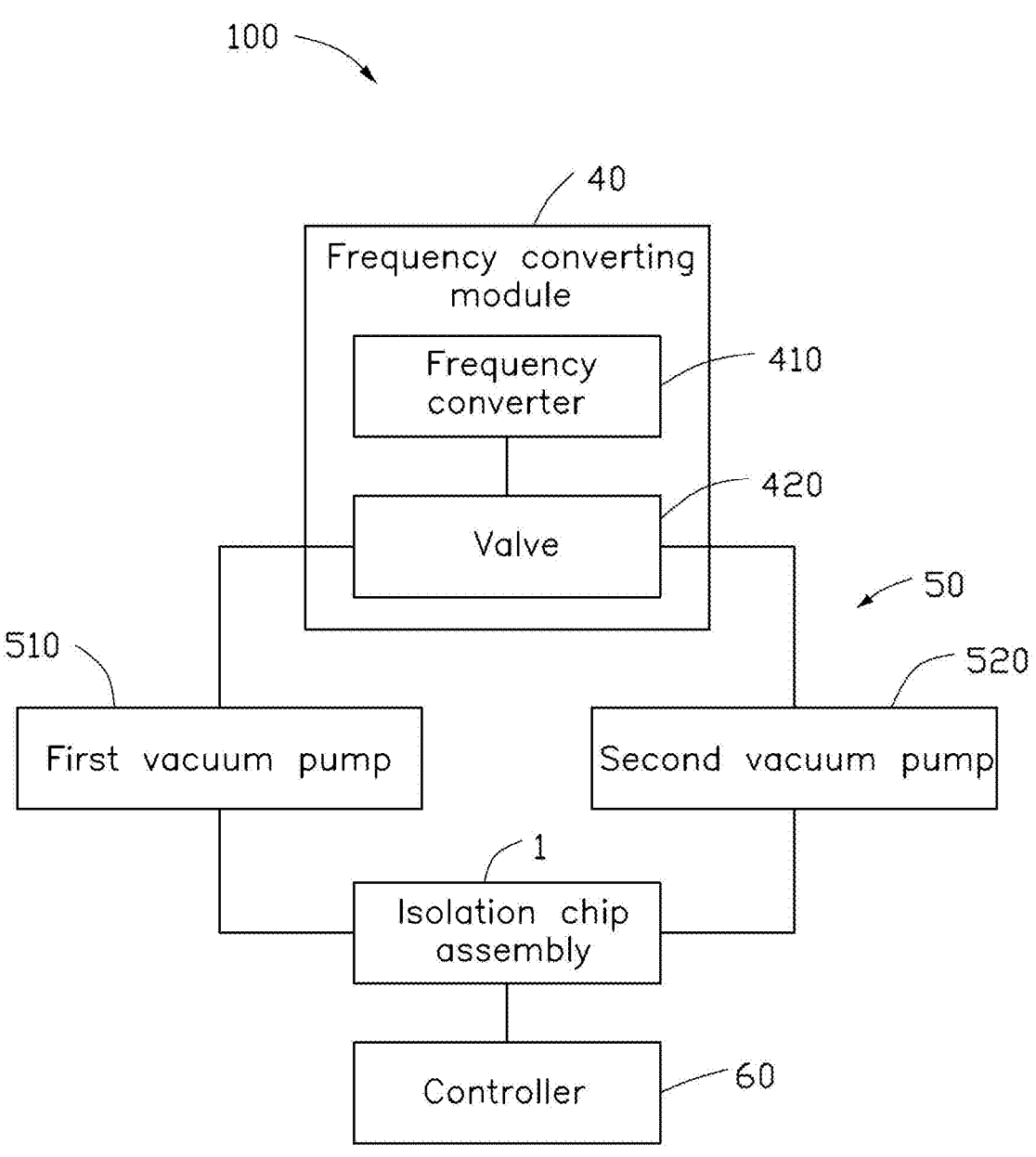
FIG. 4 is a block diagram of an embodiment of an isolation device according to the present disclosure.

FIG. 4 illustrates an embodiment of an isolation device 100 including the isolation chip assembly 1, a vacuum system 50, a frequency converting module 40, and a controller 60.

The vacuum system 50 generates the negative pressure in the first chamber 15 and the second chamber 17 of the isolation chip assembly 1 alternately. In at least one embodiment, the vacuum system 50 includes a first vacuum pump 510 and a second vacuum pump 520. The first vacuum pump 510 is connected to the first outlet 152 of the isolation chip 10. The second vacuum pump 520 is connected to the second outlet 172 of the isolation chip 10.

The frequency converting module 40 is electrically connected to the vacuum system 50, and provides electric power to the vacuum system 50. In an embodiment, the frequency converting module 40 includes a frequency converter 410 and a valve 420 connected to the frequency converter 410. The valve 420 can be an electromagnetic valve or a rotary valve. The valve 420 is alternately switched to connect one of the first vacuum pump 510 and the second vacuum pump 520, to cause the vacuum system 50 to alternately apply the negative pressure in the first chamber 15 and the second chamber 17. That is, when the valve 420 connects to the first vacuum pump 510, the frequency converter 410 controls the first vacuum pump 510 to generate the negative pressure in the first chamber 15. The compositions that have sizes smaller than the size of the pores of the first filtration membrane 14 can pass through the first filtration membrane 14 under the negative pressure. Then, the frequency converter 410 controls the first vacuum pump 510 to stop operating, and the valve 420 is switched to connect to the second vacuum pump 520. The frequency converter 410 controls the second vacuum pump 520 to apply the negative pressure in the second chamber 17. The compositions that have sizes smaller than the size of the pores of the second filtration membrane 16 can pass through the second filtration membrane 16 under the negative pressure. Then, the frequency converter 410 controls the second vacuum pump 520 to stop operating. The above procedures are repeated until complete isolation is achieved.

The controller 60 controls the first oscillator 20 and the second oscillator 30 to operate when the first chamber 15 is stopped evacuated. Thus, the first oscillation wave and the second oscillation wave are generated. The controller 60 further controls the first oscillator 20 and the second oscillator 30 to operate when the second chamber 17 is stopped evacuated. The controller 60 can be electrically connected to the first vacuum pump 510 and the second vacuum pump

7

520. When the first vacuum pump 510 or the second vacuum pump 520 stops operating, the controller 60 determines that the first vacuum pump 510 stops evacuating the first chamber 15 or the second vacuum pump 520 stops evacuating the second chamber 17. Then, the controller 60 informs the first oscillator 20 and the second oscillator 30 to start operating.

An embodiment of an isolation method of isolating target particles from a liquid sample, which is executed by the isolation chip assembly 1, is also provided. The method includes the following steps.

S1, the isolation chip assembly 1 is provided, and the liquid sample is added to the sample reservoir 13 of the isolation chip assembly 1.

S2, the first chamber 15 is evacuated through the first outlet 152 to generate the negative pressure in the first chamber 15.

In at least one embodiment, before evacuating the first chamber 15, the first outlet 152 and the second outlet 172 are connected to the vacuum system 50. Then, the vacuum system 50 evacuates the first chamber 15 through the first outlet 152, to cause the compositions having sizes that are smaller than sizes of the pores of the first filtration membrane 14 to enter the first chamber 15 through the first filtration membrane 14.

S3, vacuuming of the first chamber 15 is stopped, and the first oscillator 20 and the second oscillator 30 operate to generate the first oscillation wave and the second oscillation wave. At the same time, the second chamber 17 is evacuated through the second outlet 172 to generate the negative pressure in the second chamber 17.

The first oscillation wave drives the first filtration membrane 14 to vibrate at a high frequency. Therefore, the target particles adsorbed in the pores of the filtration membranes can be quickly separated from the pores of the filtration membranes and resuspended in the liquid sample. The second chamber 17 can prevent the target particles from gathering together. At the same time, since the negative pressure is generated in the second chamber 17, the compositions adhered on the first filtration membrane 14, which have sizes smaller than the size of the pores of the second filtration membrane 16, can return to the sample reservoir 13 together with the flows of the fluid, and further move towards the second chamber 17 through the second filtration membrane 16.

S4, vacuuming of the second chamber 17 is stopped, and the first oscillator 20 and the second oscillator 30 operate.

Then, the steps S2 to S4 can be repeated for several times, so that the components smaller than the pores of the filtration membranes in the liquid sample are removed, and the components larger than the pores of the filtration membranes are remained in the sample reservoir 13, so as to achieve better isolation and purification effect.

The present application will be described in detail in combination with specific examples and comparative examples.

EXAMPLE

The exosomes are isolated and purified from a urine sample of 2 mL by the isolation chip assembly of the present disclosure. The frequency of the first oscillator is 6250 Hz (approximately the same as the resonance frequency of the filtration membrane), and the frequency of the second oscillator is 200 Hz.

8

Comparative Example 1

Different from Example 1, the exosomes are isolated and purified from a urine sample of 2 mL by the isolation chip. The first oscillator and the second oscillator are not included in the isolation chip.

Comparative Example 2

Different from Example 1, the exosomes are isolated and purified from a urine sample of 2 mL by the isolation chip. The first oscillator is not included in the isolation chip.

Comparative Example 3

Different from Example 1, the exosomes are isolated and purified from a urine sample of 2 mL by the isolation chip. The second oscillator is not included in the isolation chip.

Comparative Example 4

The exosomes are isolated and purified from a urine sample of 2 mL by dead-end filtration. The dead-end filtration uses the same filtration membrane as the isolation chip, but the liquid sample is placed upstream of the filtration membrane. Under the function of pressure difference, components that have sizes smaller than the size of the pores of the filtration membrane are allowed to pass through the filtration membrane.

Figure 5:
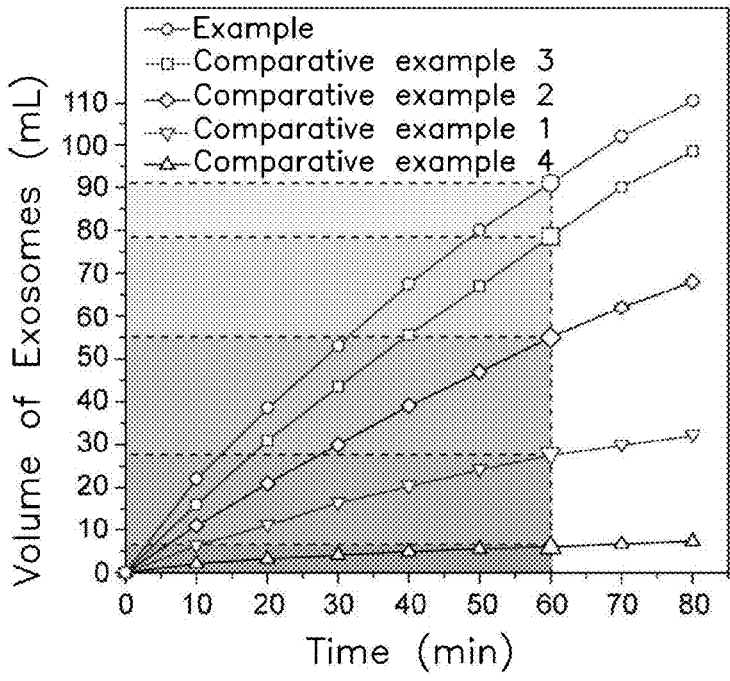
FIG. 5 is a relationship between volumes of exosomes obtained by Example and Comparative examples 1~4 and purification times.
Figure 6:
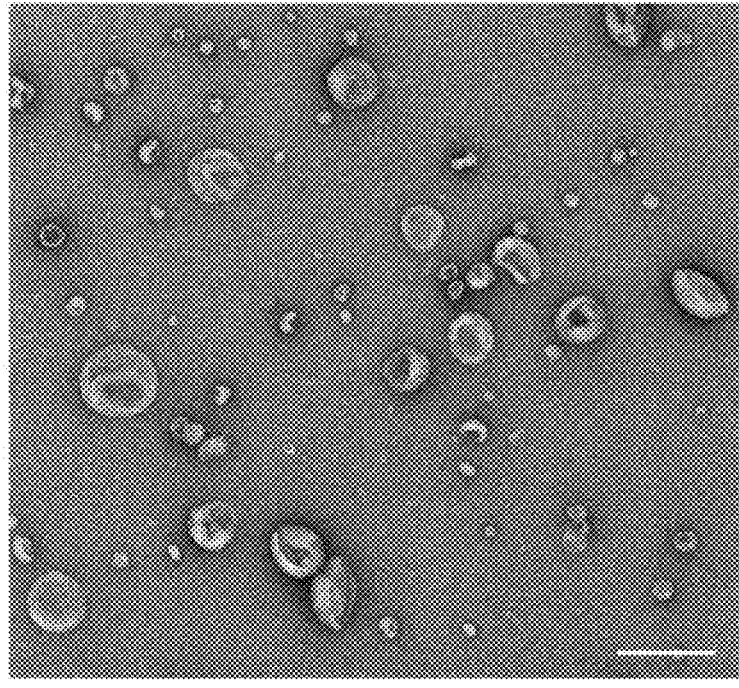
FIG. 6 is a scanning electron micrograph (SEM) of exosomes obtained by Example of the present disclosure.

The concentrations of the exosomes obtained in Example and Comparative Examples 1-4 are measured, and the results are recorded in FIG. 5. As shown in FIG. 5, the exosomes of nearly 30 μm can be isolated from the liquid sample within 10 minutes in Example, and the isolation efficiency is much higher than that in the Comparative examples 1-4. The exosomes obtained in the Example are further subjected to a transmission electron microscope test, and the test result is shown in FIG. 6 (the scale is 250 nm). FIG. 6 shows that the exosomes have a particle size of 50 nm to 200 nm, which is consistent with the theoretical size of the exosomes. The exosomes are round or cup-shaped, which have a high integrity.

Figure 7:
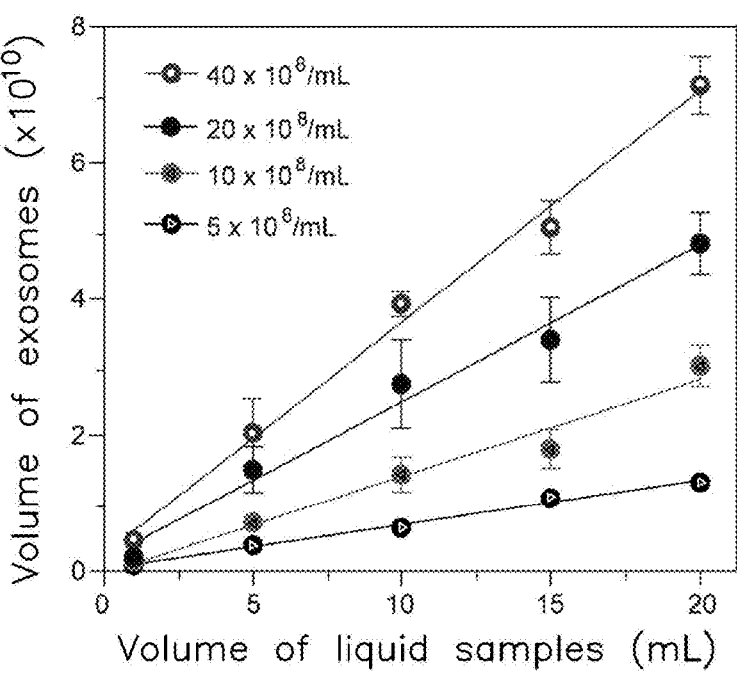
FIG. 7 is a diagram of concentrations of exosomes obtained from urine samples of different volumes and concentrations of exosomes.

Furthermore, the same isolation chip assembly is used to repeat the isolation and purification of exosomes from four urine samples. The four urine samples have different concentrations of exosomes. Each of the four urine samples has a volume of 1 mL to 20 mL. Then, an ultraviolet-visible spectrophotometer is used to test the concentrations of proteins in the exosomes, and the results are recorded in FIG. 7. As shown in FIG. 7, the concentrations of exosomes linearly increase with the increase of the volume of the urine samples, indicating that when the liquid samples having different volumes or when the liquid samples having exosomes with different concentrations are tested, the isolation chip assembly has a high structural stability during the isolation and the purification of the exosomes. In addition, the same isolation chip assembly is repeatedly used for the isolation and the purification of the exosomes from a urine sample of 10 mL. After twenty times, the coefficient of variation (CV) between the concentrations of exosomes is less than 9.9%, indicating that the isolation chip assembly has a high repeatability during the isolation and the purification of the exosomes.

Figure 8:
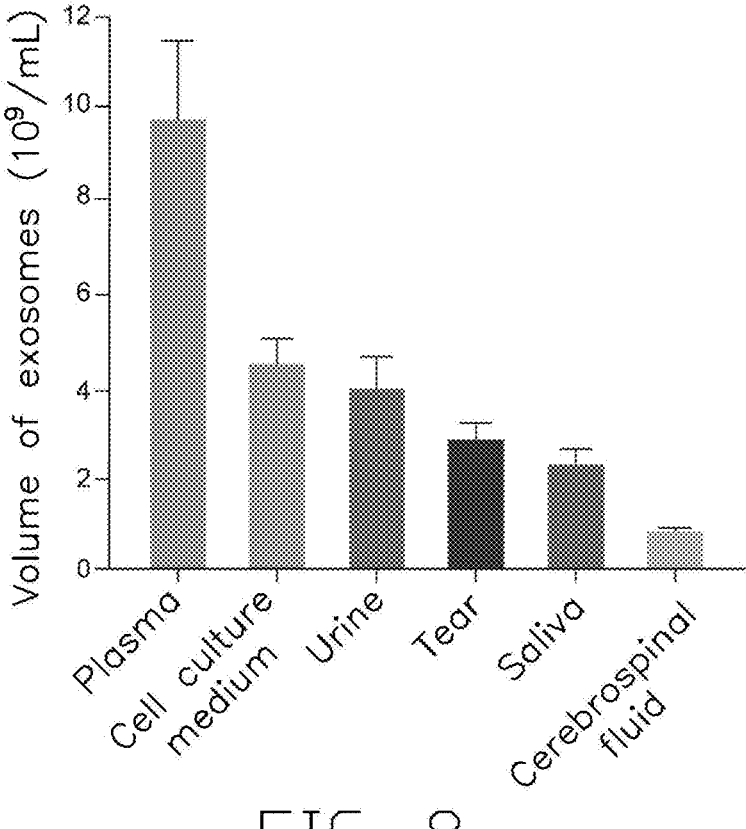
FIG. 8 is a diagram of concentrations of exosomes obtained from different types of liquid samples.

Furthermore, the isolation chip assembly is also used to isolate and purify exosomes from other liquid samples, including plasma, cell culture medium, tear, saliva, and cerebrospinal fluid (CSF). As shown in FIG. 8, higher concentrations of exosomes are obtained from these liquid samples, indicating that the isolation chip assembly is suitable for the isolation and the purification of exosomes from various liquid samples. Moreover, the size of the exosomes is also in the range of 50 nm to 200 nm.

Comparative Example 5

Existing isolation and purification methods, such as ultra-centrifugation (UC), polyethylene glycol (PEG) precipitation, phosphatidylserine (PS) affinity, size exclusion chromatography (SEC), and membrane affinity (MA), are used to isolate exosomes from the same urine sample.

Figure 9:
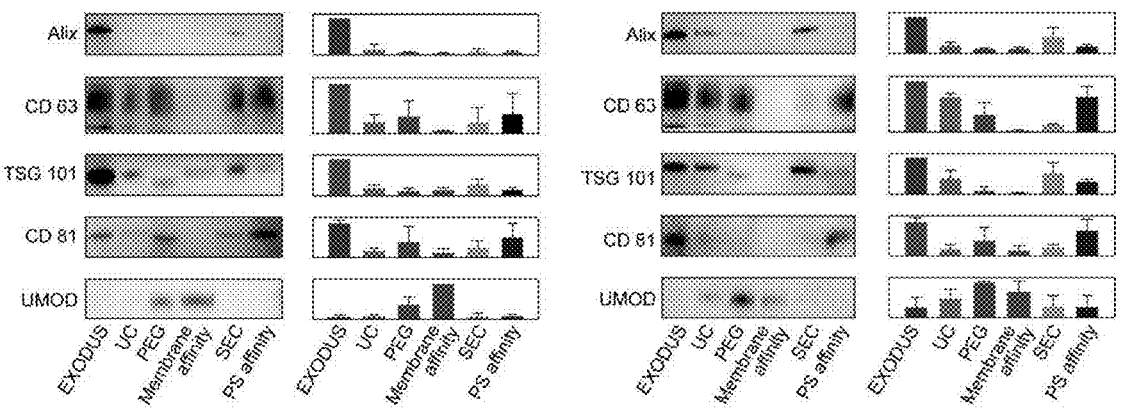
FIG. 9 is Western blot analysis of exosomes obtained by Example and Comparative example 5.

Western blotting is used to test protein markers including ALIX, CD63, TSG101, and CD81 in the exosomes obtained by Example and Comparative example 5. Uromodulin (UMOD) is a protein with a highest concentration in the urine samples, which can be used to characterize the purity of the exosomes. As shown in FIG. 9, compared with the exosomes isolated by the existing isolation and purification methods, four protein markers can be detected in the exosomes isolated and purified by the isolation chip assembly (denoted as EXODUS in FIG. 9), indicating that the purification yield is high. The exosomes do not adsorb a large amount of uromodulin, indicating that the purification accuracy is high.

Figure 10:
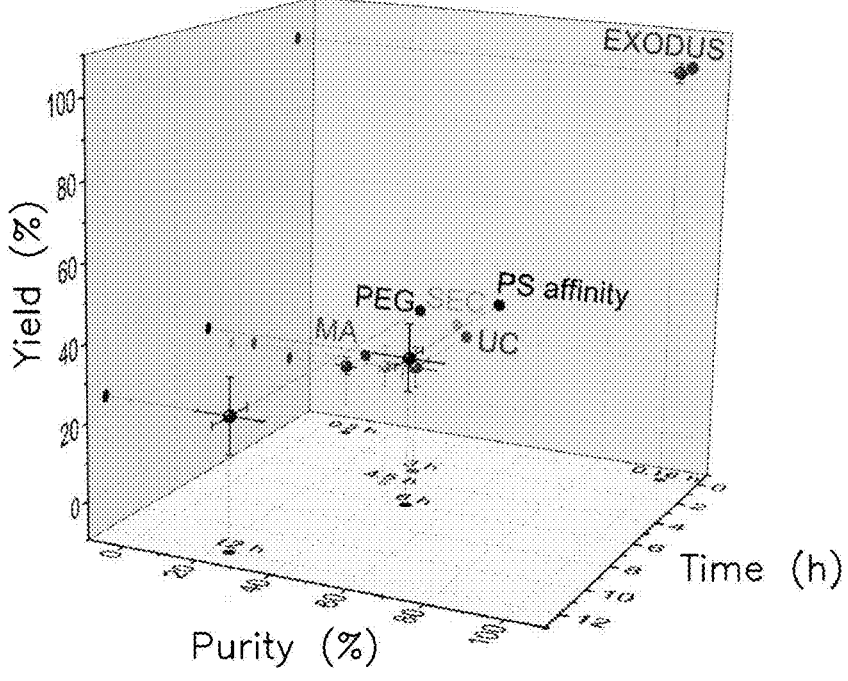
FIG. 10 is a diagram showing a comparison between Example 5 and Comparative Example 5 in three dimensions including purification time, exosomes yield, and purity of exosomes.

The purification time, the exosomes yield, and the purity of exosomes are three dimensions to characterize different isolation and purification methods. As shown in FIG. 10, compared to the existing isolation and purification methods in Comparative Example 5, the isolation chip assembly (denoted as EXODUS in FIG. 10) requires a shorter purification time (reduced by 95%), a higher exosomes yield (increased by 526%), and a higher purity of exosomes (increased by 259%), indicating that the isolation chip assembly is more competitive than the existing isolation and purification methods.

The embodiments shown and described above are only examples. Therefore, many commonly-known features and details are neither shown nor described. Even though numerous characteristics and advantages of the present technology have been set forth in the foregoing description, together with details of the structure and function of the present disclosure, the disclosure is illustrative only, and changes may be made in the detail, including in matters of shape, size, and arrangement of the parts within the principles of the present disclosure, up to and including the full extent established by the broad general meaning of the terms used in the claims. It will, therefore, be appreciated that the embodiments described above may be modified within the scope of the claims.

What is claimed is:

1. An isolation chip assembly configured for isolation and purification of target particles from a liquid sample, the isolation chip assembly comprising:
an isolation chip, wherein the isolation chip comprises a sample reservoir, a first filtration membrane, and a second filtration membrane, the first filtration membrane and the second filtration member are disposed at opposite sides of the sample reservoir, sizes of pores of each of the first filtration membrane and the second filtration membrane are configured to be smaller than sizes of the target particles, the isolation chip further comprises a first chamber and a second chamber, the first chamber is connected to the sample reservoir through the first filtration membrane, the second chamber is connected to the sample reservoir through the second filtration membrane;
first oscillators mounted on a surface of the first filtration membrane away from the sample reservoir and on a surface of the second filtration membrane away from the sample reservoir, wherein the first oscillators are configured to generate a first oscillation wave when operating; and
second oscillators mounted on an of the first chamber away from the first filtration membrane and on an outer surface of the second chamber away from the second filtration membrane, wherein the second oscillators are configured to generate a second oscillation wave when operating, wherein the first oscillators and the second oscillators are located on a same horizontal plane, a frequency of the first oscillation wave is greater than a frequency of the second oscillation wave, an amplitude of the first oscillation wave is less than an amplitude of the second oscillation wave, and the first oscillation wave and the second oscillation wave are generated such that the first oscillation wave and the second oscillation wave cooperatively disturb the liquid sample, the first filtration membrane, and the second filtration membrane to generate an acoustic streaming; wherein the frequency of the first oscillation wave is 5000 Hz to 8000 Hz, and the frequency of the second oscillation wave is 100 Hz to 500 Hz.

2. The isolation chip assembly of claim 1, wherein the frequency of the first oscillation wave is equal to a resonance frequency of the first filtration membrane or equal to a resonance frequency of the second filtration membrane.

3. The isolation chip assembly of claim 1, wherein the isolation chip further comprises a first side cover and a second side cover, the first side cover comprises a first cover body, and a first barrier sheet and a second barrier sheet located on opposite sides of the first cover body, the first filtration membrane is fixed between the first barrier sheet and the second barrier sheet, and faces the first cover body, the first cover body, the first barrier sheet, the second barrier sheet, and the first filtration membrane cooperatively define the first chamber; the second side cover comprises a second cover body, and a third barrier sheet and a fourth barrier sheet located on opposite sides of the second cover body, the third barrier sheet faces the first barrier sheet, the fourth barrier sheet faces the second barrier sheet, the second filtration membrane is fixed between the third barrier sheet and the fourth barrier sheet, and faces the second cover body, the second cover body, the third barrier sheet, the fourth barrier sheet, and the second filtration membrane cooperatively define the second chamber; the sample reservoir is disposed between the first filtration membrane and the second filtration membrane.

4. The isolation chip assembly of claim 3, wherein the second oscillators are fixed to an outer surface of the first cover body and an outer surface of the second cover body.

5. The isolation chip assembly of claim 1, wherein the first chamber defines a first outlet connecting the first chamber to an ambient environment, and the second chamber defines a second outlet connecting the second chamber to the ambient environment.

6. The isolation chip assembly of claim 1, wherein each of the first oscillators is a harmonic oscillator.

7. The isolation chip assembly of claim 1, wherein each of the second oscillators is a vibrating motor.

* * * * *